United States Patent [19]

Gonser

[11] 4,385,344
[45] May 24, 1983

[54] VISIBLE LIGHT APPARATUS FOR CURING PHOTO-CURABLE COMPOSITIONS

[75] Inventor: Donald I. Gonser, York, Pa.

[73] Assignee: Dentsply Research & Development Corp., Milford, Del.

[21] Appl. No.: 182,643

[22] Filed: Aug. 29, 1980

[51] Int. Cl.³ .................. G01J 1/00; F21V 13/08; F21V 33/00

[52] U.S. Cl. .................. 362/32; 250/504 R; 250/503.1; 362/263; 362/293; 362/804

[58] Field of Search .......... 250/504, 503; 362/32, 362/293, 263, 804

[56] References Cited

U.S. PATENT DOCUMENTS

| | | | |
|---|---|---|---|
| 624,392 | 5/1899 | Smith | 128/23 |
| 3,327,712 | 6/1967 | Kaufman et al. | 128/398 |
| 3,455,622 | 7/1969 | Cooper | 362/293 |
| 3,463,914 | 8/1969 | Lutter | 362/293 |
| 3,527,974 | 9/1970 | Cooper | 362/293 |
| 3,564,231 | 2/1971 | Bruce et al. | 240/1 |
| 3,711,700 | 1/1973 | Westland, Jr. et al. | 362/293 |
| 3,712,984 | 1/1973 | Lienhard | 362/32 |
| 3,775,606 | 11/1973 | Bazell et al. | 240/47 |
| 3,984,673 | 10/1976 | Gray | 362/293 |
| 4,025,779 | 5/1977 | Ahroni | 240/10 L |
| 4,048,490 | 9/1977 | Troue | 362/293 |
| 4,095,881 | 6/1978 | Maddox | 362/293 |
| 4,106,078 | 8/1978 | Inoue | 362/32 |
| 4,112,335 | 9/1978 | Gonser | 362/32 |
| 4,149,086 | 4/1979 | Nath | 362/32 |
| 4,206,494 | 6/1980 | Lovering | 362/293 |
| 4,229,658 | 10/1980 | Gonser | 250/504 H |
| 4,298,806 | 11/1981 | Herold | 250/504 H |

Primary Examiner—Teddy S. Gron
Attorney, Agent, or Firm—Woodcock, Washburn, Kurtz, Mackiewicz & Norris

[57] ABSTRACT

There is provided a device for efficient production of light in the low visible range for photo-curing materials, the device being particularly adapted for dental applications. The efficient light source comprises a tungsten halogen lamp with a concentrating reflector which reflects visible light and passes middle and far infrared wavelengths. A filter system is provided comprising a dichroic heat reflecting filter which efficiently passes light from 400 to 700 nm and reflects energy in the visible red and near infrared wavelengths back to the lamp envelope, thus enhancing lamp halogen cycle efficiency. The dichroic heat reflecting filter is followed by a dielectric filter which provides a high efficiency bandpass at the desired visible range. A highly efficient fiber optic light guide is positioned to receive the focused and filtered light and to transmit it to a reduced surface light applying tip at the end of a handpiece. The fiber light guide is encased in a specially designed sheathing which provides protection to the optical fibers and carries two electrical conductors which are connected between a control switch on the handpiece and the power supply for the lamp.

35 Claims, 3 Drawing Figures

VISIBLE LIGHT APPARATUS FOR CURING PHOTO-CURABLE COMPOSITIONS

BACKGROUND OF THE INVENTION

This invention lies in the field of low power visible light source apparatus and, more particularly, apparatus for providing a source of visible light for curing photo-curable compositions such as are utilized in dental work.

In the field of dentistry there have been recent developments which have increased the need for an efficient apparatus for delivering light in the visible range, and particularly the range of about 400 to 500 nanometers, to activate the polymerization of certain kinds of photo-curable compositions to produce dental sealants, dental filling materials, dental adhesives and the like. In addition, other uses for photocurable compositions, particularly as adhesives, have been and are being developed. There has thus come into being a great need for a highly efficient and reliable light source apparatus which is flexible, can be easily hand held and manipulated, and which is safe for use.

In the past, ultraviolet radiation has been used extensively as one mechanism for activating photo-curable materials. For many applications, including the dental area, it has been found that visible light curable compositions are preferred. Visible light is more efficient in crossing the boundary between two dissimilar materials, and is passing through material which has already been cured. It is preferred in many dental applications because it can pass through tooth structure. Also, recent photo-curable compositions which have excellent properties as adhesives in industry in general have been found which require visible light for curing. Still further, the operator, e.g. the dentist, can see the visible light when it is directed at a small operating surface, and this gives a degree of operator feedback which is useful in many applications.

A number of problems exist in the design of a light apparatus for curing photo-curable compositions. First, for most all applications, including the dental one, it is necessary that the apparatus be safe for operator handling. This means that stray light emission must be either eliminated or reduced to safe levels, that the light must be concentrated at a specific small area, and that the light emitted at the small area be within biologically safe limits. Further, the apparatus must be easily manipulable, leading to the demand for a small handpiece, which handpiece is light in weight and does not heat up. For this reason, there should be means for producing that light at a location somewhat remote from the point of light application, and means for guiding the light from the location where it is generated to a specific small area where the operator can irradiate the compositions which are sensitive to and cured by the visible light. There are also substantial demands placed on the optical system, whereby there is provided light essentially limited to the desired bandpass range, e.g. 400 to 500 nm. Further, in most applications it is desirable to operate the light source in an on-off mode, and this imposes requirements on the power supply functional design and the lamp itself, so as to achieve a light source which maintains specified operating characteristics and achieves a satisfactory life time.

SUMMARY OF THE INVENTION

It is an object of this invention to provide an efficient light source in the low visible range, e.g. 400 to 500 nm.

It is another object of this invention to provide an efficient light source for providing light to a specific small area, which source is biologically safe for applications in dentistry and the like.

It is another object of this invention to provide a light source which is highly efficient in delivering light in the visible range and which blocks out emission of light in much of the visible beyond 510 nanometer wavelength and including the infrared range.

It is yet another object of this invention to provide a light source of visible light, which light source includes a flexible and easily manipulated end tip for delivering light to a remote small area.

It is a still further object of this invention to provide light apparatus having control means for operating a light lamp under optimum conditions for generation of light in the visible range, and means for achieving a long life time operation of such lamp with substantially constant operating characteristics.

In view of the above objects, there is provided a light apparatus comprising a lamp source and a power supply for delivering the power thereto, the lamp and supply being positioned in an opaque housing, a filter system mounted operatively adjacent to said lamp source for filtering the lamp light and providing light in the desired visible band width range, light transmission means comprising optical fibers encased in a flexible opaque sheath for transmitting the visible light, and an opaque handpiece at the end of the sheath with means for delivering the light to a small area. The lamp is suitably a tungsten halogen lamp and is mounted in combination with a dichroic reflector which reflects and focuses light within the visible and near infrared range through about 1100 nanometers and allows passage of undesired infrared wavelengths greater than 1100 nanometers through to the back of the lamp metallic housing where heat is dissipated. A dichroic heat reflecting filter is provided just downstream from the lamp source, which reflects infrared between 700 and 1100 nanometers back at the lamp envelope, thereby enabling the envelope to reach the desired high temperature of greater than 250° C. necessary for efficient operation of the halogen cycle. A specially designed sheath is provided for giving structural support to the optical fiber light guide and for carrying electrical leads which communicate between the handpiece and the power supply. The power supply is designed to provide optimum on-off mode operation of the handpiece by ramping the lamp filament supply voltage at the predetermined rate and providing a limit on the in-surge current at the time of lamp turn-on.

DESCRIPTION OF THE PREFERRED EMBODIMENTS

Figure 1:
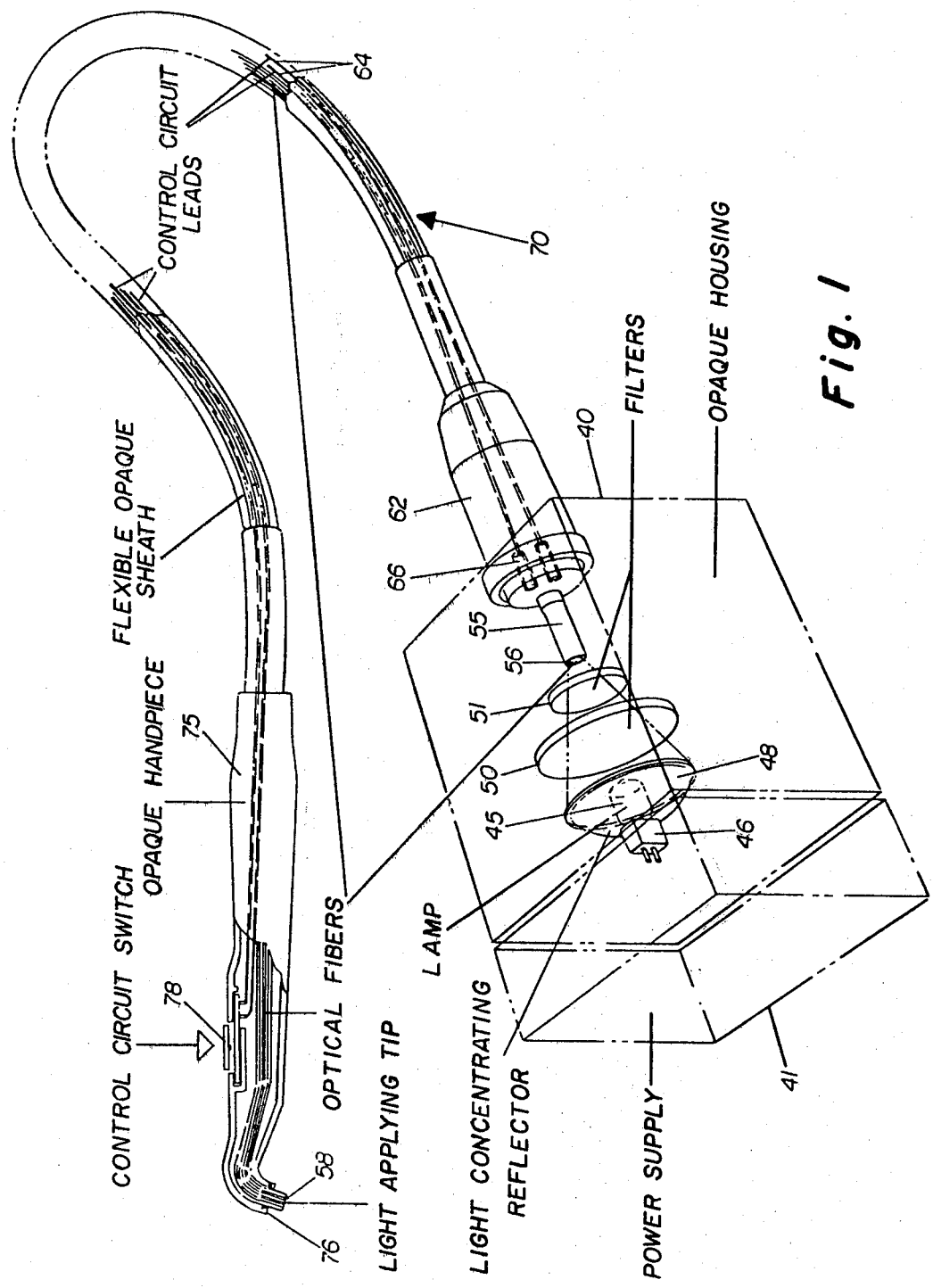
FIG. 1 is a perspective schematic view of the apparatus of this invention, showing the primary components thereof.

Referring now to FIG. 1, the drawing illustrates the main components of the light apparatus of this invention. An opaque housing 40 houses the lamp light source, which is described in detail hereinbelow. Packaged within the overall housing, but illustrated separately for purposes of clarity, is a regulated power supply 41. A lamp 45, having a mount 46 for connection to the power supply, is shown in combination with a reflector 48, for focusing light at the receiving end 56 of a light guide 55. A filter assembly comprising first filter 50 and second filter 51 is designed for two purposes, namely to achieve the desired bandpass of the light which is collected in light guide 55, and also to reflect heat back so as to aid in the operation of lamp 45, as explained hereinbelow. Filter 50 is positioned closely to the rim of reflector 48, so as to achieve a high efficiency of reflectance of heat wavelengths back to lamp 45.

Figure 3:
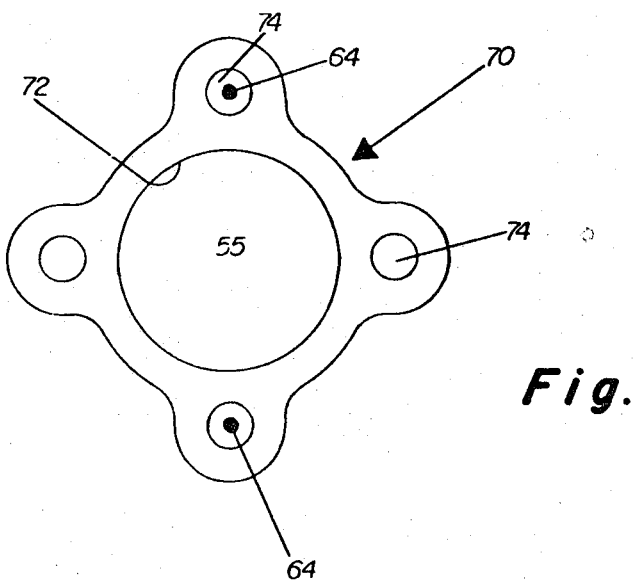
FIG. 3 is a cross sectional view showing the construction of the sheathing which carries the optic fiber light guide of this invention, as well as electrical conductor control leads for operator control of the device.

Light guide 55 has its receiving or proximal end mounted in a plug 62, which is mounted in position by conventional means not shown. Plug 62 also provides means for connecting a pair of leads 64 to the power supply, which leads connect the power supply to a control circuit switch 78 mounted within the opaque handpiece. Switch 78 provides the operator with means for turning on the light source as desired, by a momentary depression of such switch. Both the light guide 55 and the leads 64 are contained within a flexible opaque sheath 70, a cross sectional view of which is shown in FIG. 3 and discussed further in connection therewith. The distal, or far end of the light guide is brought through the opaque handpiece 75 to an end opening 76, where guide tip 58 is provided for directing the light from the guide to the desired remote location. Guide 55 is commercially available blue wavelength enhanced glass on glass fiber optic light guide, which transmits efficiently in the 400 to 500 nm range. Other fibers or materials may be utilized in guide 55, e.g. a liquid filled light guide. The invention is not limited by the construction or composition of guide 55.

Still referring to FIG. 1, a detailed examination of the components of the system provides an understanding of the means by which the overall improvement in efficiency is provided. The lamp 45 is a tungsten halogen lamp, having a rated operating voltage of 21 volts DC, but operated in this device at 23.0 volts DC. Suitably lamp source 45 is a 165 watt tungsten halogen lamp in combination with a dichroic reflector assembly 48. The tungsten halogen lamp is basically any tungsten filament lamp, with the following main parts: (1) a tungsten wire filament on a suitable mount; (2) a sealed bulb or envelope, made of quartz and containing an inert gas to protect the filament from oxidation; and (3) a base 46 which serves as a mechanical support and provides the electrical connection.

When the lamp 45 is connected to an electrical circuit, the current passing through the filament overcomes the resistance and the power consumed heats the filament to its operating temperature. One of the major advantages of a tungsten halogen lamp is the maintenance of initial light output throughout life. Such a lamp does not blacken and the bulb remains clean until burn out because of the halogen cycle. In this cycle, tungsten evaporated particles combine with iodine vapor to form tungsten iodide which is carried back from the bulb wall to the filament. The high temperature separates the original elements, with tungsten returned to the filament and iodine set free to repeat the cycle. Ordinarily, in a standard incandescent lamp, the tungsten particles evaporate from the hot filament and are carried by convection currents to the relatively cool bulb wall, where they accumulate and form a black deposit. However, when the bulb wall is in excess of 250° C., the tungsten evaporated particles and iodine vapor combine with each other to form tungsten iodide. In order to achieve this, it is necessary to maintain the bulb wall temperature in excess of 250° C. Operation of the bulb wall at temperatures above 250° C. is readily achieved in the small diameter tubular quartz envelope approximately 1 cm diameter by 1 cm long of lamp 45, such that the lamp wall is maintained clean, resulting in a much higher light output over the life of the lamp than obtained with a conventional lamp. This condition is enhanced by the filter system of this invention, particularly the heat reflecting filter 50 which reflects wavelengths between 700 and 1100 nanometers back into the source lamp via the lamp reflector.

A specular dichroic reflector 48 is integrally mounted with lamp 45. In the preferred embodiment, the reflector projects light into an aperture size of approximately 5 mm diameter at a focal distance of 2.8 cm. The specular reflector 48 is most efficient in reflecting light in the visible and near infrared range between 400 and 1100 nm wavelength, but is a poor and inefficient reflector in the infrared greater than 1100 nanometers which largely pass through the reflector substrate which is comprised of Pyrex (trademark of Corning Glass Company). A large portion of the total energy produced by the tungsten filament is in the infrared region, such that it is desirable that the middle and far infrared pass through the reflector substrate whereupon it is conveniently dissipated.

Filter 50 is a heat reflecting filter which substantially rejects wavelengths between 700 and 1100 nm and passes the desired visible light. It is made with a substrate of Pyrex (trademark of Corning Glass Company) coated with two stacks of evaporated film. The low index film is thorium floride and the high index film is zinc sulfide. For filter 50, between 420 nm and 500 nm the transmission is above 80% average and above 68% minimum; between 500 and 700 nm the transmission is less than 85% average; between 700 and 1200 nm the transmission is less than 15% average. The reflected visible red and near infrared wavelengths are passed back into the lamp envelope, thereby assisting in fast heating of the envelope up to and over a temperature of 250° C. within the short operation time of the lamp (typically 10 seconds). At the same time, reflecting the energy in the 700 to 1100 nm wavelength range back into the lamp envelope provides substantial thermal protection to the dielectric bandpass filter 51. Without operation of filter element 50 the filter 51 degrades quickly thus providing a safe failure mode due to reduced light output at all wavelengths.

The dielectric filter 51 is made with a substrate consisting of two layers of soda lime glass or other similar optically clear material. The substrate is coated with a two stack, high and low index film coating. The dielectric two stack film is then cemented together using the two soda lime glass pieces with the optical epoxy cement. A minimum clear aperture of 17 mm around a common center is maintained on the filter. The exposed faces of the filter are finally coated with an anti-reflective coating having optimum transmission between 400 nm and 500 nm wavelength. The high index film coating is suitably zinc sulfide, and the low index Cryolite. The transmission parameters of the dielectric filter are as follows: between 420 and 500 nm, greater than 85% average and greater than 70% minimum; between 520 and 850 nm, less than 5%; at 850 nm less than 5.0%; and at 900 nm less than 50% transmission.

With the above filter combination and the tungsten halogen lamp operated as specified herein, the light output delivered by the light guide in the range between 400 and 500 nanometers is approximately 430 mw/cm$^2$ at the contact surface. Filter 51 is designed to fail in a direction toward greater safety, i.e., pass a very low level of light output, by degrading should the dichroic Filter 50 either fail or not be located in its required normal position, such as an error during assembly of the product.

The color temperature of the filament of lamp 45 at the nominal voltage rating, i.e., 21 volts, is approximately 3400° Kelvin. An increase in the color temperature of the lamp by 100° K. approximately doubles the output in the range of 400 to 500 nm. Such an increase in color temperature of 100° K. is accomplished by increasing the lamp input power by about 10%, i.e., the regulated voltage is increased from 21 volts to 23.1 volts. A substantial reduction in lamp filament life is observed for a lamp which is operated at greater than 10% above its power rating, e.g. at 12% or 13% above. For this reason, it is necessary to closely regulate the lamp voltage to within 0.15% when the lamp is being operated, and also to limit the initial transient or surge current when the lamp is turned on. In the apparatus of this invention, the filament start up current is limited to no more than 12 amperes, a feature which extends lamp life considerably.

With a limit on the initial start up current to the filament, and with the requirement of operating the lamp at 110% rated power, there is a minimum time within which the lamp can be brought up to power to assure longest possible lamp life. For the apparatus of this invention, it has been found that the minimum time is suitably about 350 milliseconds. The voltage applied to the lamp cannot be ramped at a rate faster than 350 ms, in order to safely achieve turn on without excess surge current and to assure limited thermal shock to the lamp filament and lamp seals. However, there is also a desired maximum time for turning on the lamp, which has been found to be less than about 0.7 seconds, and suitably about 0.7 seconds. It has been found that when the turn on time is much greater, e.g. in the range of 1 to 2 seconds or more, the operator senses that the equipment is not functioning properly, since pressing the touch button on-off switch does not produce a corresponding light response in timely fashion. Accordingly, it is a design criteria for this apparatus that the ramping time for turning on the lamp be in the range of 0.3 to 0.7 seconds. After the turn on time, the operating current to the lamp is stabilized at approximately 7.17± 0.10 amps, at 23.0± 0.1 volts.

Figure 2:
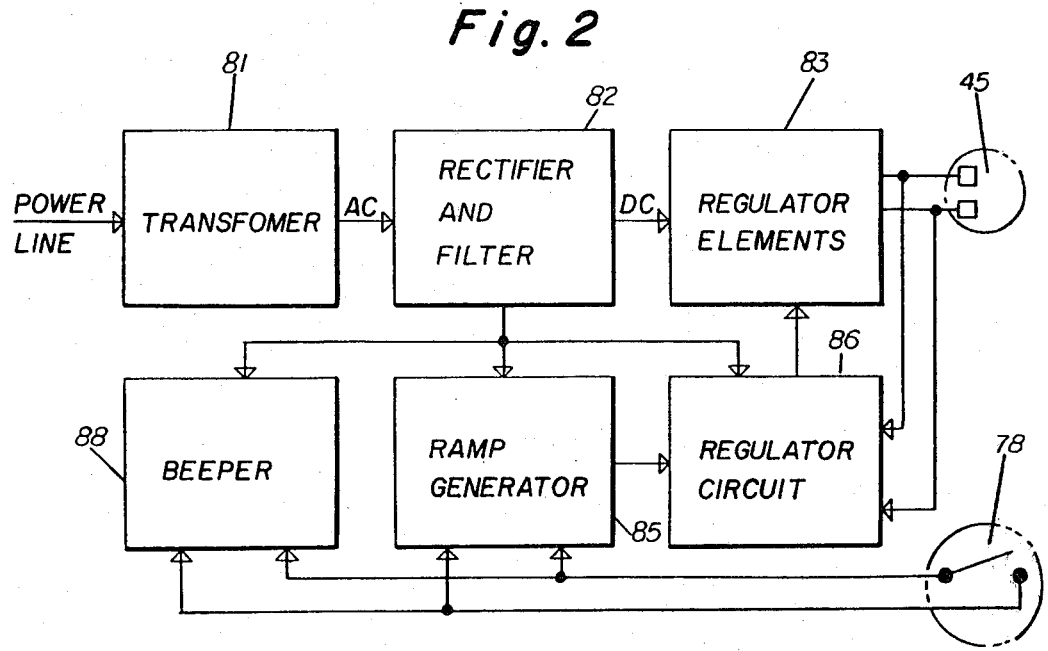
FIG. 2 is a block diagram of the power supply and sound beeper of this invention.

Referring to FIG. 2, there is shown a block diagram of the circuitry used in combination with the tungsten halogen lamp in the preferred embodiment of the apparatus of this invention. It is to be understood that this block diagram is illustrative only, and the invention is not restricted to the precise circuit design used to achieve the control voltages and current limitations. Regulator circuits are well known, and applicant makes no claim to the design of the circuits as such, but only to the combination of the circuits for generating filament drive voltages, and current limitations, together with the optical system of the apparatus.

Power is taken from a power line and passed through a transformer 81 which steps the voltage down to the level desired. The AC voltage is rectified and filtered at block 82, to provide an unregulated DC which is connected in series with regulator elements 83. In the preferred embodiment, block 83 comprises three 2N-3055 pass transistors connected in parallel, which transistor combination limits the current delivered to the lamp 45 to 12 amps. The output voltage of block 83 is connected in a voltage feedback loop to regulator circuit 86, of conventional design. Closing of switch 78 triggers ramp generator 85, which generates the desired ramp from 0 voltage to 110% rated voltage within a time period of 0.3 to 0.7 seconds. The output of the ramp generator is connected to the regulator circuit, which provides an amplified ramp signal to the regulator elements, and then provides a regulated DC to the lamp after full voltage has been reached. The switch 78 which starts the ramp generator is also connected to sound beeper 88, which is a conventional switching oscillator for generating an audible beeping sound after a predetermined time period has elapsed following initiation of light output. In the preferred embodiment, by way of illustration, the sound beeper provides an 0.25-second signal after the light has been on for 9.75 seconds, thereby informing the operator that the light has been used for a desired length of time.

Referring now to FIG. 3, there is shown a cross-sectional view of the flexible opaque sheath which is utilized in the apparatus of this invention. As illustrated, the preferred sheath is a 5-bore tubing. The large center bore 72 carries the light fibers 55. Positioned peripherally around the opening 72, axially extending ridges, or ribs, containing smaller bores about 0.06 inches in diameter, each suitable for carrying one of the leads 64. The ridges, including any ones which do not carry wires, give the sheath compression resistance. The sheath is made of a suitable thermal plastic insulation material, such as polyvinyl chloride. The five bore configuration as illustrated provides very good strain relief and compression resistance, thus offering suitable protection to the optical fiber light guide 55, and at the same time gives good protection to the electrical conductors 64. As illustrated, only two of the smaller bores carry wires, but any combination of them may be used to carry wires.

It is thus seen that there is provided a light source apparatus which is highly flexible in providing a desired concentration of visible light to a small defined surface at a remote location. The optical system comprising the tungsten halogen lamp, and the dichroic reflector and filter assembly in combination with the characteristics of the light guide, provide a highly efficient light source which delivers power at a desired density, and which effectively and safely filters out undesired wavelengths. The light output delivered from the light guide at the tip, for the range of 400 to 500 nm, is approximately 430 mw/cm$^2$ at contact. The infrared power delivered from the light delivery end of the guide is less than 400 mw/cm$^2$ at contact, which is within safe biological limits.

The invention has been illustrated in terms of a preferred embodiment for dental applications, but is not limited to the configuration which has been found to be best for that application. Other uses require different bandwidths of useful light than the 400–500 nm bandwidth. Such other bandwidths of output light are obtained by altering the bandpass characteristics of the filter system while maintaining the disclosed means of reflecting red and/or infrared wavelengths back to the lamp for improved operation thereof. Likewise, while the apparatus of this invention provides particular efficiency for use in the on-off mode, it is also adapted for continuous operation.

I claim:

1. Light source apparatus for delivering light confined to a limited bandwidth of visible light, comprising:
   a. a tungsten halogen light source enclosed in an envelope, and means for energizing said light source;
   b. filter assembly means for filtering light produced by said source, said filter assembly means having a first means for reflecting red and infrared light back to said envelope and transmitting visible light within a first predetermined bandwidth, and a second means for transmitting visible light within a second predetermined bandwidth; and
   c. guide means for collecting light transmitted by said second means and delivering said light to a location remote from said source.

2. The light apparatus as described in claim 1, wherein said light source comprises a tungsten halogen lamp and a reflector integrally mounted with said lamp for focusing light, said reflector having the property of reflecting visible light and near infrared light and passing wavelengths greater than about 1100 nm.

3. The light apparatus as described in claim 1, wherein said first means of said filter assembly means comprises a dichroic heat reflecting filter.

4. The light apparatus as described in claim 3, wherein said dichroic heat reflecting filter has a high reflectivity in the range of 700 to 1100 nm.

5. The light apparatus as described in claim 1, wherein said second means of said filter assembly means comprises a dielectric filter.

6. The light apparatus as described in claim 5, wherein said dielectric filter has a bandpass of about 400 to 500 nm.

7. The light apparatus as described in claim 2, wherein said first means of said filter assembly means comprises a dichroic heat reflecting filter and said second means of said filter assembly means comprises a dielectric filter, and said dichroic heat reflecting filter is positioned between said dielectric filter and said light source.

8. The light apparatus as described in claim 7, wherein said dichroic heat reflecting filter has a high reflectivity in the range of 700 to 1100 nm, and said dielectric filter has a bandpass of about 400 to 500 nm.

9. The light apparatus as described in claim 8, wherein said guide means has the property of low transmission of wavelengths below 400 nm, and an opaque flexible sheathing having a large center bore within which said guide means is contained.

10. The light apparatus as described in claim 9, wherein said guide means comprises glass fibers.

11. The light apparatus as described in claim 9, wherein said guide means comprises plastic fibers.

12. The light apparatus as described in claim 9, wherein said guide means comprises a liquid filled light guide.

13. The light apparatus as described in claim 9, comprising a handpiece connected to the end of said guide means, said handpiece having a light applying tip opening from which the end of said light guide extends for delivery of visible light.

14. The light apparatus as described in claim 13, wherein said handpiece has a switch means for switching on said energizing means.

15. The light apparatus as described in claim 14, wherein said switch means is a finger actuated momentary switch means.

16. The light apparatus as described in claim 14, comprising control wires carried by said sheathing, which control wires connect said switch means to said energizing means for control thereof.

17. The light apparatus as described in claim 16, wherein said sheathing has a ridge extending axially along the outer circumference of said sheathing.

18. The light apparatus as described in claim 17, wherein said ridge contains a small bore adapted for carrying said control wires in electrical isolation from one another.

19. The light apparatus as described in claim 16, wherein said sheathing has a plurality of ridges extending axially along the outer circumference of said sheathing.

20. The light apparatus as described in claim 19, wherein the number of said ridges is four.

21. The light apparatus as described in claim 19, wherein one of said ridges contains a small bore adapted for carrying said control wires in electrical isolation from one another.

22. The light apparatus as described in claim 20, wherein one of said ridges contains a small bore adapted for carrying said control wires in electrical isolation from one another.

23. The light apparatus as described in claim 19, wherein two or more of said ridges each contains a small bore adapted for carrying said control wires.

24. The light apparatus as described in claim 20, wherein two or more of said ridges each contains a small bore adapted for carrying said control wires.

25. The light apparatus as described in claim 1, wherein said light source has a rated power of about 150 watts and said energizing means comprises means for energizing said light source at a power level of about 165 watts.

26. The light apparatus as described in claim 1, wherein said energizing means comprises means for energizing said light source lamp at 10% above its rated power.

27. The light apparatus as described in claim 1, including means for initiating energization by said energizing means, and wherein said energizing means comprises ramp means for ramping power to said source over a predetermined time period, said period being within the range of about 0.3 second to about 0.7 second.

28. The light apparatus as described in claim 27, wherein said energizing means comprises means for limiting current to said lamp during said ramp energization.

29. A light source apparatus for generating a concentrated light beam, said apparatus having a tungsten halogen lamp and means for energizing same, characterized by (a) a dichroic filter positioned forward of said lamp, said filter having a bandpass of about 400 to 700 nm and a high reflectivity in the range of about 700 to 1100 nm, whereby energy in said reflectivity range is reflected back to said lamp while energy within said bandpass is passed; and (b) a reflector positioned backward of said lamp, for focusing light at a focal point forward of said lamp, said reflector reflecting a high percentage of light in the range of about 400 to 1100 nm and passing a high percentage of light above about 1100 nm.

30. The light source apparatus as described in claim 29, wherein said lamp has an envelope which must be kept at a temperature of at least about 250° C. to maintain the halogen cycle in said lamp.

31. The light source apparatus as described in claim 30, wherein said lamp has a design power rating and where said energizing means raises said lamp to said design power rating in less than one second.

32. The light source apparatus as described in claim 30, wherein said lamp envelope has a cylindrical suraface with a diameter of about 1 cm and a length of about 1 cm.

33. A light source apparatus for generating a concentrated light beam, said apparatus having a tungsten halogen lamp and means for energizing same, said lamp having an envelope which must be maintained above a temperature of at least 250° C., said apparatus being characterized by:
   a. means for operating said source in an on-off mode;
   b. a reflector means mounted operatively relative to said lamp so as to reflect light from said lamp and concentrate said reflected light at a predetermined focal point, said reflector means having the property of reflecting a high percentage of light having wavelengths in a range below a predetermined wavelength and passing a high percentage of light having wavelengths greater than said predetermined wavelength;
   c. a filter positioned in the path of said concentrated light, said filter having a characteristic of passing light within a first predetermined range and a reflectance characteristic of reflecting light within a second predetermined range back toward said lamp, whereby light reflected from said filter is dissipated as heat in said lamp envelope; and
   d. light guide means for collecting and guiding light, having a receiving end positioned at said focal point.

34. Light source apparatus for delivering light confined to a limited bandwidth of visible light, comprising:
   a. a tungsten halogen light source enclosed in an envelope;
   b. filter assembly means for filtering light produced by said source, said filter assembly means having a first means for reflecting red and infrared light back to said envelope and transmitting visible light within a first predetermined bandwidth, and a second means for transmitting visible light within a second predetermined bandwidth;
   c. reflector means mounted integrally with said lamp for focusing light at a focal point forward of said lamp, said reflector means reflecting light in a first range of wavelengths and passing a high percentage of light having wavelengths above said first range;
   d. guide means positioned at said focal point for collecting light reflected by said reflector means and delivering said light to a location remote from said source; and
   e. light source energizing means for energizing said light source, said energizing means comprising means for bringing said light source up to rated power within about 0.3 to 0.7 seconds.

35. The light source apparatus as described in claim 34, wherein said light source envelope has a substantially cylindrical surface with a diameter of about 1 cm and a length of about 1 cm.

* * * * *